United States Patent
Niewczas et al.

(10) Patent No.: US 10,488,420 B2
(45) Date of Patent: *Nov. 26, 2019

(54) METHODS OF DIAGNOSING AND PREDICTING RENAL DISEASE

(71) Applicant: Joslin Diabetes Center, Inc., Boston, MA (US)

(72) Inventors: Monika A. Niewczas, Boston, MA (US); Andrzej S. Krolewski, Needham, MA (US)

(73) Assignee: Joslin Diabetes Center, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/711,073

(22) Filed: Sep. 21, 2017

(65) Prior Publication Data

US 2018/0011109 A1 Jan. 11, 2018

Related U.S. Application Data

(63) Continuation of application No. 13/130,711, filed as application No. PCT/US2009/067366 on Dec. 9, 2009, now Pat. No. 9,791,452.

(60) Provisional application No. 61/177,074, filed on May 11, 2009, provisional application No. 61/121,398, filed on Dec. 10, 2008.

(51) Int. Cl.
*G01N 33/68* (2006.01)

(52) U.S. Cl.
CPC ... *G01N 33/6863* (2013.01); *G01N 2333/525* (2013.01); *G01N 2333/5412* (2013.01); *G01N 2800/042* (2013.01); *G01N 2800/347* (2013.01)

(58) Field of Classification Search
None
See application file for complete search history.

(56) References Cited

U.S. PATENT DOCUMENTS

2010/0173936 A1 7/2010 Khan et al.

OTHER PUBLICATIONS

Niewczas et al "Serum Concentrations of Markers of TNFalpha an Fas-Mediated Pathways and Renal Function in Nonproteinuric Patients with Type 1 Diabetes" (Clin J Am Soc Nehrol 2009 vol. 4: pp. 62-70, published online Dec. 10, 2008). (Year: 2008).*
Rosolowsky, et al., "Between hyperfiltration and impairment: Demystifying early renal functional changes in diabetic nephropathy" Diabetes Research and Clinical Practice, Published on-line Oct. 11, 2008, vol. 82s, pp. s46-s53.
Niewczas, et al., "Serum Concentrations of Markers of TNFx and Fas-Mediated Pathways and Renal Function in Nonproteinuric Patients with Type 1 Diabetes" Clinical Journal Am Soc Nephrol, 2009, vol. 4, pp. 62-70 (XP-002683004).
Knight, Eric L., et al., "Kidney Dysfunction, Inflammation, and Coronary Events: A Prospective Study", J. Am. Soc. Nephrol., 2004, vol. 15, pp. 1897-1903.
Lin et al., The association of serum lipids and inflammatory biomarkers with renal function in men with type II diabetes mellitus, Kidney International, 2006, vol. 69, pp. 336-342.
Ng, D.P.K., et al., "Reduced GFR and albuminuria in Chinese type 2 diabetes mellitus patients are both independently associated with activation of the TNF-x system", Diabetologia, Oct. 2008, vol. 51, pp. 2318-2324.
Tonelli, et al. "Biomarkers of inflammation and progression of chronic kidney disease" Kidney International; 2005; vol. 68; pp. 237-245.
Keller, et al. BMC Nephrology; 2008; vol. 9; pp. 1-9.
Liu, et al. "Predictive and pathogenetic value of plasma biomarkers for acute kidney injury in patients with acute lung injury" Crit. Care Med.; 2007; vol. 35; No. 12; pp. 2755-2761.
Rosolowsky, et al. "Between hyperfiltration and impairment: Demystifying early renal functional changes in diabetic nephropathy" Diabetes Research and Clinical Practice; 2008; vol. 82; pp. S46-S53.
Lin, et al. "The association of serum lipids and inflammatory biomarkers with renal function in men with type II diabetes mellitus" International Society of Nephrology; Kidney International; 2006; vol. 69; pp. 336-342.
Ankersmit, et al. "Impaired T cell proliferation, increased soluble death-inducing receptors and activation-induced T cell death in patients undergoing haemodialysis" Clinical Exp. Immunol. 2001; vol. 125; pp. 142-148.

* cited by examiner

*Primary Examiner* — Catherine S Hibbert
(74) *Attorney, Agent, or Firm* — Pierce Atwood LLP; Kevin M. Farrell

(57) ABSTRACT

This disclosure relates to methods of diagnosing and predicting renal disease, using one, two, or more biomarkers, including sTN-FR1, sTNFR2, sFAS, TNF, and IL-6.

3 Claims, 4 Drawing Sheets

■ Normoalbuminuria (NA)  ■ Microalbuminuria (MA)

TNFα

IL6 sTNFR1 sFas

METHODS OF DIAGNOSING AND PREDICTING RENAL DISEASE

CLAIM OF PRIORITY

This application claims priority under 35 USC § 119(e) to U.S. Provisional Patent Application Ser. No. 61/177,074, filed on May 11, 2009, and U.S. Provisional Patent Application Ser. No. 61/121,398, filed on Dec. 10, 2008, the entire contents of which are hereby incorporated by reference.

FEDERALLY SPONSORED RESEARCH OR DEVELOPMENT

This invention was made with Government support under Grant No. DK-41526 awarded by the National Institutes of Health. The Government has certain rights in the invention.

TECHNICAL FIELD

This disclosure relates to methods of diagnosing and predicting early renal function decline (ERFD), using biomarkers sTNFR1, sTNFR2, sFAS, TNF, and IL-6.

BACKGROUND

The traditional model of the development of end-stage renal disease (ESRD) in type 1 diabetes (T1DM), in which microalbuminuria (MA) leads to proteinuria and then proteinuria is followed by renal function loss, has been challenged recently. Increase in urinary albumin excretion is an important determinant of diabetic nephropathy progression, but it does not entirely explain this phenomenon. For example, the loss of renal function commences earlier than previously recognized and precedes the onset of proteinuria (Perkins et al., J Am Soc Nephrol. 18:1353-1361, 2007). A longitudinal study of T1DM (the 1st Joslin Study of Natural History of Microalbuminuria) showed that renal function decline began with the onset of MA in about one third of patients and progressed in a linear fashion from normal kidney function to renal insufficiency (Perkins et al., 2007, supra). In addition, renal function decline occurred in a noticeable proportion of patients with T1DM and normal albumin excretion (Perkins et al., 2007, supra; Caramori et al., Diabetes 52:1036-1040, 2003).

SUMMARY

As shown herein, progressive early renal function decline (ERFD), e.g., in type 1 diabetes (T1DM) and type 2 diabetes begins while glomerular filtration rate (GFR) is in the normal or elevated range and before onset of proteinuria. Inflammation and apoptosis may be involved in this process. The present methods can be used to identify diabetic subjects with early renal function decline, based on serum markers of the TNF pathway (e.g., TNFα, sTNFR1, and sTNFR2), the Fas pathways (e.g., sFas), and IL-6. The present methods can also be used to identify or predict diabetic subjects at risk for developing end stage renal disease (ESRD), based on serum or plasma markers of the TNF pathway (e.g., sTNFR1).

In some embodiments, the present disclosure provides methods for determining (e.g., predicting or diagnosing) whether a human subject has an increased risk of developing early renal function decline (ERFD). These methods can include obtaining a sample from a human subject who has normoalbuminuria (NA), microalbuminuria (MA), or proteinuria (PT), and measuring the levels of one or more (including all) biomarkers selected from the group consisting of TNFa, soluble TNF receptor type 1 (sTNFR1), soluble TNFR2 (sTNFR2), soluble Fas (sFas), and interleukin-6 (IL-6), in the subject sample. These measured levels can then be compared with suitable reference levels of the one or more biomarkers. In some aspects, this comparison, or observations obtained from such a comparison, can be used to determine whether the subject has an increased risk of developing ERFD. For example, a difference between the levels of the one or more biomarkers in the subject sample and the reference levels can indicate that the subject has an increased risk of developing ERFD. In some cases, the difference can be that the levels of the one or more biomarkers in the subject sample are higher (e.g., significantly higher) than the reference levels of the same biomarkers. In some instances, the subject sample can include serum from the subject. In some cases, the subject can be a subject with diabetes, e.g., Type 1 or Type 2 diabetes. For example, the subject can be selected because they have diabetes, e.g., Type 1 or 2 diabetes. Furthermore, the subject can be a subject with normoalbuminuria, microalbuminuria, or proteinuria. For example, the subject can be selected because they have normoalbuminuria, microalbuminuria, or proteinuria. Methods for identifying subjects with normoalbuminuria, microalbuminuria, or proteinuria are known in the art and are disclosed below. In some instances, biomarkers measured in subjects with Type 1 diabetes can include, e.g., sTNFR1, sTNFR2, and sFas; TNFa, sTNFR1, sTNFR2, and sFas; or TNFa, sTNFR1, sTNFR2, sFas, and IL-6. In some instances, biomarkers measured in subjects with Type 2 diabetes can include, e.g., TNFa, sTNFR1, sTNFR2, sFas, and IL-6. In some instances, the human subject can be a subject that does not present any clinical signs or symptoms of chronic heart disease (CHD) or ischemic heart disease. Furthermore, in some cases, the human subject can be a subject that has a glomerular filtration rate (GFR) of 90 mL/minute or more.

In some embodiments, the present disclosure provides methods for determining whether a human subject has an increased risk of developing chronic kidney disease (CKD), or end stage renal disease (ESRD), or both. Such methods can include obtaining a sample from a human subject who has proteinuria, and measuring the level of soluble TNF receptor type 1 (sTNFR1) in the subject sample. These measured levels can then be compared with suitable reference levels (e.g., a reference levels of sTNFR1). In some aspects, this comparison, or observations obtained from such a comparison, can be used to determine whether the subject has an increased risk of developing CKD, ESRD, or both. For example, a difference between the levels of the sTNFR1 in the subject sample and the reference levels can indicate that the subject has an increased risk of developing CKD, ESRD, or both. In some cases, the difference can be that the levels of the sTNFR1 in the subject sample are higher (e.g., significantly higher) than the reference levels. In some instances, the human subject can be a subject with Type 1 or Type 2 diabetes. In some instances, the human subject can be a subject with Type 1 diabetes and/or proteinuria.

Unless otherwise defined, all technical and scientific terms used herein have the same meaning as commonly understood by one of ordinary skill in the art to which this disclosure belongs. Methods and materials are described herein for use in the present disclosure; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DETAILED DESCRIPTION

Figure 1A:
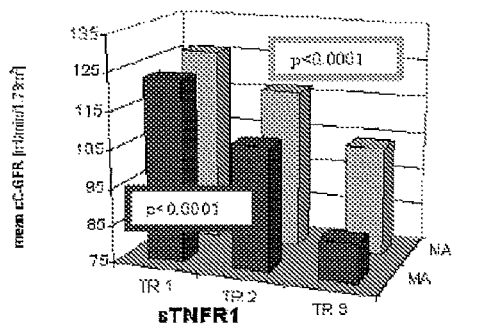
FIGS. 1A-1F are 3-D bar graphs showing mean cC-GFR in the study population of individuals with type 1 diabetes according to albuminuria status (NA=normoalbuminuria and MA=microalbuminuria) and tertile (T1, T2, T3) of an inflammatory marker: 1A, sTNFR1; 1B, sTNFR2; 1C, TNFα; 1D, sFas; 1E, sICAM-1; 1F, IP10). P value for trend across the tertiles in NA (light grey bars) and in MA (dark grey bars), respectively.
Figure 1B:
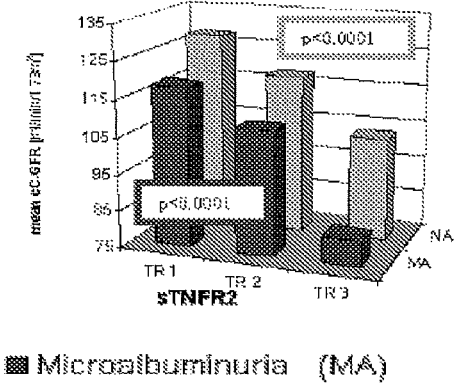
Figure 1C:
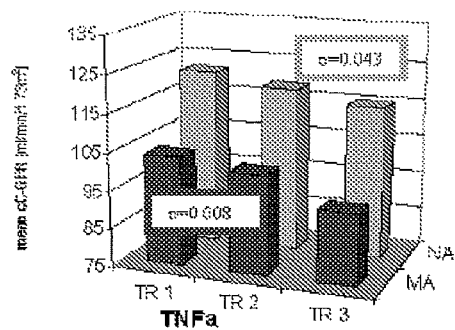
Figure 1D:
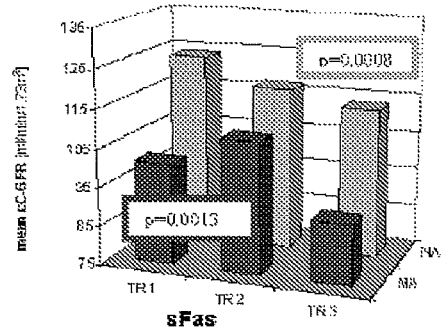
Figure 1E:
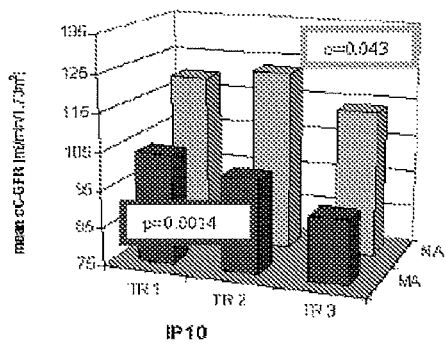
Figure 1F:
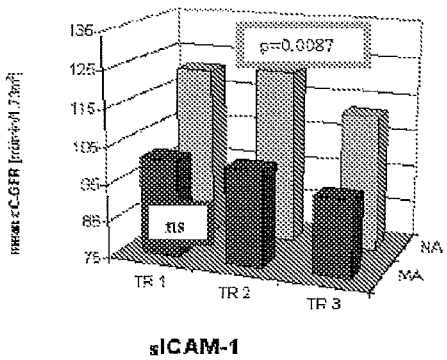

Low-grade chronic inflammation is thought to be involved in the pathogenesis of diabetic nephropathy (Navarro et al., Cytokine. Growth Factor. Rev. 17:441-450, 2006, and Galkina et al., J. Am. Soc. Nephrol., 17:368-377, 2006). Tumor necrosis factor alpha (TNFα/TNF) is a key mediator of inflammation and plays a role in apoptosis. In animal models, its effects on kidneys include reduced glomerular filtration rate (GFR) and increased albumin permeability (Navarro, supra). TNFα mediates its signal via two distinct receptors, tumor necrosis factor receptor 1 (TNFR1) and tumor necrosis factor receptor 2 (TNFR2), which are membrane-bound and also present in soluble form in serum (Macewan et al., Cell. Signal., 14:477-492, 2002). TNFα mediates its inflammatory effects by induction of a broad spectrum of chemokines including interleukin 8 (IL8); monocyte chemotactic protein-1 (MCP1); interferon gamma inducible protein 10 (IP-10) and adhesion molecules such as intercellular adhesion molecule-1 (ICAM-1) and vascular adhesion molecule-1 (VCAM-1) (Segerer et al., J. Am. Soc. Nephrol., 11:152-176, 2000; Wong et al., Clin. Exp. Immunol., 149:123-131, 2007).

The Fas pathway mediates apoptosis and may play a role in the progression of diabetic nephropathy (Kumar et al., Nephron. Exp. Nephrol., 96:e77-e88, 2004; Kumar et al., Mol. Cell. Biochem., 259:67-70, 2004; Schelling et al., Lab. Invest., 78:813-824, 1998; and Perianayagam et al., J. Lab. Clin. Med., 136:320-327, 2000). The binding of Fas ligand (FasL) to Fas, its membrane-bound receptor which is also present in serum in soluble form (sFasL, sFas), leads to an apoptotic response (Baba et al., Nephrology, 9:94-99, 2004 and Ortiz et al., Nephrol. Dial. Transplant., 14:1831-1834, 1999).

Interleukin-6 (IL-6) is a pleiotropic, proinflammatory cytokine that has been associated with complications in diabetes. Specifically, cross-sectional studies of subjects with type 2 diabetes demonstrate that elevated serum levels of Il-6 are associated with diabetic nephropathy (Shikano et al., Nephron., 85:81-5, 2000). However, a similar association between 11-6 and diabetic nephropathy has not been reported for type 1 diabetes (Schram et al., Diabetologia., 48:370-8, 2005; Niewczas et al., Clin J Am Soc Nephrol., 4:62-70, 2009).

The majority of studies on serum markers of TNFα-mediated inflammation and apoptosis in diabetic nephropathy have explored their association with MA and proteinuria rather than with GFR (Zoppini et al., J. Clin. Endocrinol. Metab., 86:3805-3808, 2001).

The large cross-sectional study described herein investigated whether serum concentrations of markers including the TNFα and TNF-related markers (sTNFR1, sTNFR2, sICAM-1, sVCAM-1, IL8, MCP1, IP10), involved in Fas-related apoptosis (sFasL and sFas), IL-6, and CRP, are associated, independently from albuminuria, with variation in renal function in patients with T1DM who do not have proteinuria or advanced renal function impairment. This knowledge will facilitate the development of new diagnostic tools for identifying patients with early renal function decline and help the search for intervention protocols for high-risk patients that may be more effective if implemented 5-10 years earlier in the disease course.

The studies described herein also investigated whether serum concentrations of TNFR1 are associated with GFR in subjects with various stages of chronic kidney disease (CKD) and whether such an association can be used as a predictive marker of ESRD in such subjects.

In these studies, glomerular filtration rate was estimated by a cystatin C-based formula (cC-GFR) that was previously shown to be an accurate way of evaluating renal function in patients with diabetes (Macisaac et al., Diabet. Med., 24:443-448, 2007 and Perkins et al, J. Am. Soc. Nephrol., 16:1404-1412, 2005).

In some embodiments, the present disclosure provides methods of determining whether a subject is predisposed to develop early renal function decline (ERFD). These methods can include generating a subject profile by obtaining a biological sample, e.g., a urine or blood (e.g., serum and/or plasma) sample, from the subject, measuring the level of at least one biomarker described herein in the sample, and comparing the level of the biomarker in the urine or blood sample with a predetermined reference profile. A reference profile can include a profile generated from one or more subjects who are known to be predisposed to develop ERFD (e.g., subjects in a study who later develop ERFD), and/or a profile generated from one or more subjects who are not predisposed to develop ERFD. A "predisposition to develop ERFD" is a significantly increased risk of developing ERFD, e.g., the subject is statistically more likely to develop ERFD than a "normal" subject (e.g., a subject who has diabetes but does not have an increased risk of developing ERFD). In some aspects, a subject with a predisposition to develop ERFD is one whose sample contains one or more of the biomarkers disclosed herein in amounts that differ (e.g., significantly differ) from, or are above, below, greater than or equal to, less than or equal to, or about the same as, depending on whether the reference represents a normal risk subject or a high risk subject, from the level of the same one or more biomarkers in a reference profile. In some cases, the difference in the levels of the one or more biomarkers can be e.g., about a factor of two or at least about a factor of two (e.g., at least twice or half the level of the biomarker present in the reference profile), wherein the reference profile represents a subject who is not predisposed to develop ERFD.

In some embodiments, the subject can have one or more risk factors for developing ERFD, e.g., duration of diabetes, elevated hemoglobin A1c (HbA1c) levels (e.g., above 8.1% or above 9%), age over 35 years, elevated plasma cholesterol levels, high mean blood pressure, elevated albumin to creatinine ratio (e.g., above about 0.6), and hyperglycemia (e.g., blood glucose of over about 200 mg/dL). In some embodiments, the subject can have microalbuminuria (e.g., excretes 30-300 µg/min albumin). In another aspect, the subject may not have microalbuminuria and/or is a subject with normoalbuminuria (e.g., excretes about less than 30 µg/min) and/or has normal renal function (e.g., has serum creatinine levels at less than 1.2 mg/dl). In some embodiments, the subject can have type 1 or type 2 diabetes. Alternatively or in addition, the subject can be non-diabetic. In some embodiments, the subject can have proteinuria, e.g., macroalbuminaria (e.g., the subject excretes more than about 300 µg/min albumin). In some embodiments, the subject does not have, does not have a diagnosis of, or does not present any clinical signs or symptoms of, chronic heart disease (CHD). In some embodiments, the subject does not have, does not have a diagnosis of, or does not present any clinical signs or symptoms of, ischemic heart disease.

In some embodiments, the present disclosure provides methods of determining whether a subject is predisposed to develop end stage renal disease (ESRD). These methods can include generating a subject profile by obtaining a biological sample (e.g., a urine or blood (e.g., serum) sample) from the subject, measuring the level of at least one biomarker described herein in the sample, and comparing the level of the biomarker in the urine or blood sample with a predetermined reference profile. In some embodiments, these methods include generating a subject profile by obtaining a biological sample (e.g., a urine or blood (e.g., serum) sample) from the subject, measuring the level of TNFR1 in the sample, and comparing the level of TNFR1 sample with a predetermined TNFR1 reference profile. Reference profiles can include a profile generated from one or more subjects who are known to be predisposed to develop ESRD (e.g., subjects in a study who later develop ESRD), and/or profiles generated from one or more subjects who are not predisposed to develop ESRD. A "predisposition to develop ESRD" is a significantly increased risk of developing ESRD, i.e., the subject is more likely to develop ESRD than a "normal" subject, i.e., a subject who has diabetes but does not have an increased risk of developing ESRD. In some embodiments, a subject with a predisposition to develop ESRD is one whose sample has a listed biomarker (e.g., TNFR1) in amounts that significantly differ from, or are above, below, greater than or equal to, less than or equal to, or about the same as the level of the same biomarker in the reference profile, depending on whether the reference represents a normal risk subject or a high risk subject. In some cases, the difference in the levels of the one or more biomarkers can be, e.g., about a factor of two or at least about a factor of two (e.g., at least twice or half the level of the biomarker present in the reference profile), wherein the reference profile represents a subject who is not predisposed to develop ESRD.

In some embodiments, the subject can have one or more risk factors for developing ESRD. Such factors can include, but are not limited to, e.g., duration of diabetes, elevated hemoglobin A1c (HbA1c) levels (e.g., above 8.1% or above 9%), age over 35 years, elevated plasma cholesterol levels, high mean blood pressure, elevated albumin to creatinine ratio (e.g., >0.6), and hyperglycemia (e.g., blood glucose of over 200 mg/dL). In some embodiments, the subject can have normal kidney function (e.g., GFR=90 mL/min or more). In some embodiments, the subject can have chronic kidney disease (CKD) (e.g., stage 1 CKD (e.g., GFR=90 mL/minute or more)), stage 2 CKD (e.g., GFR=60 to 89 mL/minute), stage 3 CKD (e.g., GFR=30 to 59 mL/minute), stage 4 CKD (e.g., GFR=15 to 29 mL/min), or stage 5 CKD (e.g., GFR=less than 15 mL/min or on dialysis). In some embodiments, the subject has proteinuria (e.g., excretion greater than or equal to 300 µg/min albumin). In some embodiments, the subject has CKD (e.g., stage 1, 2, 3, 4, or 5 CKD) and proteinuria. In some embodiments, the subject has diabetes (e.g., type 1 or type 2 diabetes). In some embodiments, the subject is a non-diabetic.

In some embodiments, the methods can include measuring the level of a plurality of the biomarkers described herein, e.g., one or more biomarkers (e.g., 2, 3, 4, 5, or all of the biomarkers) can be measured. The level(s) of the biomarker(s) can be used to generate a biomarker profile for the subject.

The methods described herein can also include obtaining a sample from a subject, e.g., a blood or urine sample, and determining the level of the biomarker(s) in the sample.

In some embodiments, the methods include normalizing for urine creatinine concentrations.

The methods described herein can include contacting a sample obtained from a subject with biomarker-specific biomolecules, e.g., an array of immobilized biomarker-specific biomolecules, and detecting stable or transient binding of the biomolecule to the biomarker, which is indicative of the presence and/or level of a biomarker in the sample. The subject biomarker levels can be compared to reference biomarker levels obtained from reference subjects. Reference biomarker levels can further be used to generate a reference profile from one or more reference subjects. In one aspect, the biomarker-specific biomolecules are antibodies, such as monoclonal antibodies. In another aspect, the biomarker-specific biomolecules are antigens, such as viral antigens that specifically recognize the biomarkers. In yet another aspect, the biomarker-specific biomolecules are receptors (e.g., the TNF receptor).

The disclosure also features a pre-packaged diagnostic kit for detecting a predisposition to ERFD. The kit can include biomarker-specific biomolecules as described herein and instructions for using the kit to test a sample to detect a predisposition to ERFD. The kit can also be used to determine the efficacy of a therapy administered to prevent ERFD by contacting the biomarker-specific biomolecules with a sample obtained from a subject undergoing a selected therapy. The level of one or more biomarkers in the sample can be determined and compared to the level of the same one or more biomarkers detected in a sample obtained from the subject prior to, or subsequent to, the administration of the therapy. Subsequently, a caregiver can be provided with the comparison information for further assessment.

Biomarkers

In some embodiments, the methods described herein include the measurement of levels of certain soluble biomarkers, including one or more of sTNFR1, sTNFR2, sFAS, TNF, and IL-6. Specific alterations in one or more of the biomarkers listed herein are statistically related to the development of ERFD. These biomarkers serve as early biomarkers for disease, and characterize subjects as at high risk for future disease. The systematic names of the molecules are as follows:

TNFa: Tumor Necrosis Factor; TNF (TNF superfamily, member 2); Entrez GeneID: 7124; mRNA: NM_000594.2; protein: NP_000585.2.

soluble TNF Receptor type 1 (sTNFR1): soluble Tumor Necrosis Factor Receptor Subfamily, member 1A; sTNFRSF1A; Entrez GeneID: 7132; mRNA: NM_001065.2; protein: NP_001056.1; see also WO9531544; Fernandez-Botran et al., FASEB J. 5(11): 2567, 1991; and US2006039857.

soluble TNF receptor type 2 (sTNFR2): soluble Tumor Necrosis Factor Receptor Subfamily, member 1B; sTNFRSF1B; Entrez GeneID: 7133; mRNA: NM_001066.2; protein: NP_001057.1; see also WO9531544; Fernandez-Botran et al., FASEB J. 5(11): 2567, 1991; and US2006039857.

soluble Fas (sFas): soluble Tumor Necrosis Factor Receptor Superfamily, member 6 (sTNFRSF6); Entrez GeneID: 355; mRNA: NM_000043.3, NM_152871.1, NM_152872.1, NM_152873.1, NM_152874.1, NM_152875.1, NM_152876.1, or NM_152877.1; Protein: NP_000034.1, NP_690610.1, NP_690611.1, NP_690612.1, NP_690613.1, NP_690614.1, NP_690615.1, or NP_690616.1. See also U.S. Pat. No. 5,652,210; Chen et al., Science, 263:1759-1762, 1994; Hachiya et al., and WO 96/01277.

Interleukin-6 (IL6); Entrez GeneID; 3569; mRNA: NM_000600.3; Protein: NP_000591.1.

In some embodiments, other markers, e.g., urinary or serum biomarkers, of renal failure can also be used, as are known in the art.

A "subject" level can also be referred to as a "test" profile. A subject level can be generated from a sample taken from a subject prior to the development of microalbuminuria (e.g., when the subject is excreting less than 30 mg of albumin a day or has an albumin-creatinine (A/C) ratio of less than 30 in a random urine specimen). Thus, a "subject" level is generated from a subject being tested for predisposition to DN.

A "reference" level can also be referred to as a "control" level. A reference level can be generated from a sample taken from a normal individual or from an individual known to have a predisposition to ERFD, or from an individual known to have ESRD and/or CKD. The reference level, or plurality of reference levels, can be used to establish threshold values for the levels of, for example, specific biomarkers in a sample. A "reference" level includes levels generated from one or more subjects having a predisposition to ERFD, levels generated from one or more subjects having ESRD and/or CKD, or levels generated from one or more normal subjects.

A reference level can be in the form of a threshold value or series of threshold values. For example, a single threshold value can be determined by averaging the values of a series of levels of a single biomarker from subjects having no predisposition to ERFD. Similarly, a single threshold value can be determined by averaging the values of a series of levels of a single biomarker from subjects having a predisposition to ERFD. Thus, a threshold value can have a single value or a plurality of values, each value representing a level of a specific biomarker, detected in a urine sample, e.g., of an individual, or multiple individuals, having a predisposition to ERFD.

As described herein, a subject level can be used to identify a subject at risk for developing ERFD based upon a comparison with the appropriate reference level or levels. Subjects predisposed to having ERFD can be identified prior to the development of microalbuminuria or with microalbuminuria by a method described herein. For example, a subject level of a biomarker described herein detected in a sample from a subject can be compared to a "reference" level of the same biomarker detected in a sample obtained from a reference subject. If the reference level is derived from a sample (or samples) obtained from a reference subject having a predisposition to ERFD, then the similarity of the subject level to the reference level is indicative of a predisposition to ERFD for the tested subject. Alternatively, if the reference level is derived from a sample (or samples) obtained from a reference subject who does not have a predisposition to ERFD, then the similarity of the subject level to the reference level is not indicative of a predisposition to ERFD for the tested subject. As used herein a subject level is "similar" to a reference level if there is no statistically significant difference between the two levels. In some embodiments, a subject level differs significantly from the reference level of the same biomarker(s), when the reference level is from a reference subject who does not have a predisposition to ERFD, is indicative of a predisposition to ERFD in the subject.

In some embodiments, the biomarker for ERFD can include one or more of, e.g., TNFα, sTNFR1, sTNFR2, Fas, and IL-6, including any combination of TNFα, sTNFR1, sTNFR2, Fas, and IL-6. In some embodiments, the biomarker for ERFD can include TNFα, sTNFR1, sTNFR2, Fas, and IL-6.

In some embodiments, the biomarker for end stage renal disease (ESRD) can include sTNFR1.

Methods of Detection

Any method known in the art for determining levels of an analyte in a biological sample can be used. An exemplary biochemical test for identifying levels of biomarkers employs a standardized test format, such as the Enzyme Linked Immunosorbent Assay (ELISA) (see, e.g., *Molecular Immunology: A Textbook*, edited by Atassi et al.; Marcel Dekker Inc., New York and Basel 1984, for a description of ELISA tests). In some embodiments, the biochemical test can include a multiplex particle-enhanced immunoassay with a flow cytometry based detection system (e.g., LUMINEX®).

It is understood that commercial assay kits (e.g., ELISA) for various cytokines and growth factors are available. For example, ELISA kits are available from R&D systems. sFas can be measured, e.g., using the Quantikine Human sFas Immunoassay from R&D Systems. Arrays and chips known in the art can also be used.

EXAMPLES

The invention is further described in the following examples, which do not limit the scope of the invention described in the claims.

Example 1: Concentrations of Markers of TNFα and Fas-mediated Pathways and Renal Function in Non-proteinuric Patients with Type 1 Diabetes Characteristics of the Study Population The study group was selected from the population attending the Joslin Clinic, a major center for the treatment of patients of all ages with T1DM or T2DM. The population is about 90% Caucasian, and most reside in eastern Massachusetts. Detailed descriptions of the Joslin Clinic population and the recruitment protocol for this study have been published previously (Rosolowsky et al., Clin. J. Am. Soc. Nephrol., 2008). Eligibility criteria included residence in New England, diabetes diagnosed before age 40 years, treatment with insulin, current age 18-64 years, diabetes duration 3-39 years, and multiple measurements in the preceding two-year interval of hemoglobin A1c (HbA1c) and urinary albumin-to-creatinine ratio (ACR). For each patient, the measurements of HbA1c were summarized by the mean, and the measurements of ACR by the median. Exclusion criteria included proteinuria (median ACR ≥250 for men and ≥355 µg/min for women), ESRD, other serious illness, extreme obesity (body mass index >40 kg/m$^2$), or a median HbA1c less than 6.5% (near normoglycemia).

Trained recruiters administered a structured interview and brief examination to eligible patients at a routine visit to the clinic, the enrollment visit. The interview solicited the history of diabetes and its treatment, other health problems, and use of medications. The recruiter measured seated blood pressure twice (five minutes apart) with an automatic monitor (Omron Healthcare, Inc) and averaged them to reduce variability and also obtained samples of blood and urine.

Current and past use of medications (particularly ACE inhibitors, Angiotensin II Receptor Blockers, and other antihypertensive drugs) was recorded during the enrollment interview and supplemented by examination of clinic records to confirm prescription dates. All archived clinical laboratory measurements of HbA1c, ACR and serum cholesterol were also extracted. Details of the assays used were described previously (Ficociello et al., Clin J. Am. Soc. Nephrol., 2:461-469, 2007, and Krolewski et al., N. Engl. J. Med., 332:1251-1255, 1995). ACR values were converted to Albumin Excretion Rate (AER) according to a formula published previously (Krolewski, supra). For characterizing patients' recent exposures, repeated measures were summarized by their median (AER) or mean (HbA1c, cholesterol, lipids).

Enrollment blood samples were drawn by venipuncture into sterile collection tubes (SST Plus BD Vacutainer) (BD, NJ, USA), centrifuged at 3600 rpm for 10 minutes at 6° C. (Centrifuge 5810 R, USA) and then aliquoted into 1.5 ml sterile, non-toxic non-pyrogenic tubes cryogenic tubes (CRYOTUBES™ CRYOLINE™ System) [NUNC™ Serving Life Science, USA] and frozen at −80° C. until further analysis. Length of storage, defined as the interval between the dates of sample collection and assay-determination (range 2 to 5 years), was included as a covariate in the analysis to estimate the extent of degradation of each analyte during storage.

Serum cystatin C concentration (Dade Behring Diagnostics) was assayed on a BN PROSPEC™ System nephelometer (Dade Behring Incorporated, Newark, Del., USA). The range of detection was 0.30 to 7.50 mg/L, and the reported reference range for young, healthy persons was 0.53 to 0.95 mg/L. The intra-individual coefficient of variation for subjects with diabetes was 3.8 and 3.0 percent in samples from the lowest and highest quartiles of the cystatin C distribution, respectively (Perkins et al., J. Am. Soc. Nephrol., 18:1353-1361, 2007).

The estimated glomerular filtration rate (cC-GFR ml/min) is the reciprocal of cystatin C (mg/L) multiplied by 86.7 and reduced by subtracting 4.2. This formula was recently developed by MacIsaac et al., supra, as a reliable estimate of GFR in patients with diabetes. The method used for measuring cystatin-C was similar with respect to assay, equipment, and coefficient of variation as that reported by MacIsaac, supra.

The study group included 667 participants: 304 with MA and 363 with normoalbuminuria. Selected characteristics at their enrollment are summarized in Table 1 according to AER group. In the NA group, the 25th, 50th and 75th percentiles of the AER distribution (11, 15, and 21 µg/min) were centered in the NA range (<30 µg/min)], but in the MA group these AER percentiles (45, 69, 131 µg/min) were entirely in the lower half of the MA range (30-300 µg/min). In comparison with the NA group, the MA group had an older age, higher proportion of men, longer duration of diabetes, higher HbA1c and significantly lower cC-GFR. The difference in cC-GFR between the two study groups was clearer when renal function was grouped into categories, the latter two of the four corresponding to mild and moderate renal function impairment, present in 36% of the MA group but only in 10% of the NA group.

TABLE 1

Characteristics of the study group according to albuminuria status.

| Characteristics | NORMO-ALBU-MINURIA (n = 363) | MICRO-ALBU-MINURIA (n = 304) | P |
|---|---|---|---|
| AER* (µg/min) | 15 (11-21) | 69 (45-131) | by design |
| Age (yrs) | 39 ± 12 | 41 ± 12 | <0.05 |
| Male (%) | 44% | 61% | <0.0001 |
| Diabetes duration (yrs) | 20 ± 9 | 23 ± 10 | <0.0001 |
| HbA1c† (%) | 8.3 ± 1.2 | 8.6 ± 1.5 | <0.01 |
| cC-GFR‡ (ml/min/1.73 m$^2$) | 118 ± 24 | 99 ± 27 | <0.0001 |
| cC-GFR categories: | | | |
| >130 ml/min | 30% | 10% | |
| 90-130 | 61% | 54% | |
| 60-89 | 9% | 28% | |
| <60 | 1% | 8% | |

Data are mean ± standard deviation or median (quartiles) or %.
*AER: median albumin excretion rate during the preceding 2-year window
†HbA1c: mean hemoglobin A1c during the preceding 2-year window
‡cC-GFR: estimated glomerular filtration rate based on serum cystatin-C To distinguish the relative contributions of AER and various clinical characteristics to the large variation in renal function within the study group, the NA and MA groups were divided at the group-specific median cC-GFR (115 and 101 nil/min, respectively) into groups with higher and lower cC-GFR (Table 2). The median (25th, 75th percentiles) of the resulting distributions of cC-GFR in the NA groups were 136 (125, 148) and 102 (92, 109) ml/min and in the MA groups were 115 (108, 124) and 82 (64, 91) ml/min. All of the characteristics in Table 2 were significantly different between NA and MA groups, but many were not significantly different between the groups with higher and lower cC-GFR (two-way ANOVA). For example, the expected associations of higher HbA1c, systolic blood pressure and serum cholesterol with MA were present, as were the associations of cigarette smoking and treatment with an ACEi or ARB. However, none of these characteristics were associated with lower cC-GFR. In contrast, older age and longer diabetes duration were significantly associated with both MA and lower cC-GFR, as was evidence of medical attention represented by treatment with antihypertensive or lipid lowering agents.

TABLE 2

Characteristics of the study group according to albuminuria status and group-specific median cC-GFR.

| Characteristic | NORMOALBUMINURIA | | MICROALBUMINURIA | | GROUP CONTRAST | |
|---|---|---|---|---|---|---|
| | cC-GFR >115 (n = 183) | cC-GFR <115 (n = 180) | cC-GFR >101 (n = 152) | cC-GFR <101 (n = 152) | AER P* | cC-GFR P† |
| AER (μg/min) | 13 (10-18) | 18 (12-23) | 56 (42-100) | 85 (51-161) | By Design | <0.0001 |
| Age (y) | 37 ± 11 | 40 ± 13 | 36 ± 12 | 45 ± 11 | <0.05 | <0.0001‡ |
| Diabetes duration (y) | 19 ± 9 | 21 ± 10 | 20 ± 9 | 26 ± 9 | <0.0001 | <0.0001‡ |
| HbA1c (%) | 8.3 ± 1.2 | 8.3 ± 1.2 | 8.7 ± 1.6 | 8.4 ± 1.4 | <0.005 | ns |
| BMI (kg/m$^2$) | 25.6 ± 3.6 | 26.7 ± 4.3 | 27.2 ± 4.8 | 27.7 ± 5.2 | <0.0005 | <0.05 |
| Systolic BP (mmHg) | 118 ± 12 | 120 ± 13 | 124 ± 12 | 125 ± 15 | <0.0001 | ns |
| ACEI or ARB Rx (%) | 18% | 21% | 49% | 55% | <0.0001 | ns |
| Anti-hypertensive Rx (%) | 7% | 16% | 14% | 30% | <0.001 | <0.0001 |
| Serum Cholesterol (mg/dl) | 183 ± 29 | 181 ± 29 | 190 ± 33 | 193 ± 30 | <0.0001 | ns |
| Lipid lowering Rx (%) | 24% | 34% | 31% | 42% | <0.05 | <0.005 |
| Current smoker (%) | 9% | 12% | 19% | 18% | <0.005 | ns |

Data are mean ± standard deviation or median (quartiles) or %.
*P-value for the albuminuria main effect in an ANOVA
†P-value for the cC-GFR main effect in an ANOVA;

Serum Markers of Inflammation or Apoptosis and Impaired Renal Function

All markers were measured by immunoassay. Samples were thawed, vortexed and centrifuged, and measurements were performed in the supernatant. sTNFR1, sTNFR2 and IL-6 were measured using enzyme-linked immunoadsorbent assay (ELISA) (DRT100, DRT200 and high sensitive immunoassay HS600B, respectively) (R&D, Minneapolis, Minn., USA) according to the manufacturer's protocol. Interleukin-6 (IL-6) was measured in only a subset of the study group (156 individuals). The serum concentrations of the other protein markers were measured in a multiplex assay run on the Luminex platform. This is a multiplex particle-enhanced, sandwich type, liquid-phase immunoassay with laser-based detection system based on flow cytometry. Adipokine-panel B (HADK2-61K-B) [Linco-Milipore, USA] was used to measure TNFα; human Sepsis-Apoptosis Panel (HSEP-63K) [Linco-Milipore, USA] was used to measure sFas, sFasL, sICAM-1 and sVCAM-1; and Beadlyte® Human Multi-Cytokine Detection (48-011) [Upstate-Milipore, USA] with protocol B was used to measure IL8, IP10, MCP1. Protocols provided by vendors were followed. Briefly, the method included use of 96-well filter plates [Milipore, USA], the capture antibodies specific for each analyte bound covalently to fluorescently labeled microspheres, biotinylated detection antibodies and streptavidin-phycoerythrin. Detection incorporates two lasers and a high-tech fluidics system [Luminex 100S, Austin, Tx, USA]. Values of median fluorescence intensity were fitted to a 5-parameter logistic standard curve (Gottschalk et al., Anal. Biochem., 343:54-65, 2005).

Assay sensitivities were: TNFα, 0.14 pg/ml; sTNFR1 and sTNFR2, 0.77 pg/ml; sFas, 7 pg/ml; sFasL, 6 pg/ml; sICAM-1, 30 pg/ml; sVCAM-1, 33 pg/ml; IL8, 0.7 pg/ml; IP10, 1.2 pg/ml; MCP1, 1.9 pg/ml; IL-6, 0.04 pg/ml. If required, samples were diluted (sTNFR1, sTNFR2, sFAS, sFASL, sICAM-1, and sVCAM-1). The number of freeze-thaw cycles was one for all measurements of TNFα, IL8, IP10, MCP1 and for the majority of measurements of the other analytes. The number did not exceed two for any measurement.

Two internal serum controls were prepared in the same manner as study samples and were stored in a large number of aliquots at −80° C. Aliquots of the two controls were included in each assay (Aziz et al., Clin. Diagn. Lab. Immunol., 5:755-761, 1998) for estimating the inter-assay CV. For most assays, inter-assay CV was between 8.5% and 15.8% (15.8% TNFα, 13.0% sTNFR1, 12.7% sTNFR2, 8.5% sFas, 13.5% sFasL, 8.1% sVCAM-1, and 14.7% IP10). It was higher for the remaining three (25.2% sICAM-1, 33.3% IL8, and 28.4% MCP1). Immunoassay for TNFα, sFas and sFasL detects the free form of the protein, whereas ELISA for sTNFR1 and sTNFR2 detects the total amount of protein, free and bound with their ligand TNFα, (information provided by manufacturer).

Serum concentrations of markers of inflammation or apoptosis were examined in the same manner as the characteristics shown in Table 2. Four markers (sTNFR1, sTNFR2, sFas, and sICAM-1) were significantly associated both with AER and with cC-GFR (Table 3). TNFα and IP-10) were significantly associated only with cC-GFR group and two (IL-8 and CRP) were significantly associated only with AER group.

Analyses were done in SAS (SAS Institute, Cary, N.C., version 9.1.3). T-tests and Chi-square tests with alpha=0.05 were used for continuous variables and frequencies, respectively. Analyses in Tables 2 and 3 and FIG. 1 were ANOVAs for unbalanced design. Linear regression with cC-GFR as dependent variable was used for multivariate analysis. AER and serum concentrations of the markers were transformed to their logarithms for analysis. Missing data for serum markers never decreased the study sample by more than 5% in any model, so no remedial action was taken.

For the six markers significantly associated with cC-GFR in Table 3, the patterns of association are illustrated in FIGS. 1A-F. Separately for the NA and MA groups, patients were grouped according to the tertiles of the distribution of each marker, and the mean cC-GFR for each subgroup was depicted as a vertical bar. In both AER groups, the decrease in cC-GFR with increasing marker concentration was steepest for sTNFR1 and sTNFR2. The pattern was similar for TNFα but the differences among subgroups were smaller. For all three markers, the decrease appears steeper in the MA group than in the NA group. For the remaining three markers (sICAM-1, IP10 and sFas), a pattern of differences among subgroups was less apparent.

TABLE 3

Serum concentrations of markers of inflammation or apoptosis according to AER group and cC-GFR above or below median

| | | NORMOALBUMINURIA | | MICROALBUMINURIA | | GROUP CONTRAST | |
|---|---|---|---|---|---|---|---|
| | | cC-GFR >115 (n = 182) | cC-GFR <115 (n = 181) | cC-GFR >101 (n = 152) | cC-GFR <101 (n = 152) | AER P* | cC-GFR P† |
| | | TNF-mediated pathway | | | | | |
| TNFα | pg/ml | 3.6 (2.3, 4.8) | 3.9 (2.8, 5.8) | 4.0 (2.6, 5.4) | 4.8 (3.3, 6.4) | ns | <0.005 |
| sTNFR1 | ng/ml | 1.2 (1.0, 1.4) | 1.4 (1.2, 1.7) | 1.4 (1.2, 1.6) | 2.0 (1.6, 2.5) | <0.0001 | <0.0001 |
| sTNFR2 | ng/ml | 2.1 (1.7, 2.6) | 2.6 (2.1, 3.6) | 2.3 (1.9, 2.9) | 3.2 (2.5, 5.4) | <0.0001 | <0.0001 |
| | | Potential downstream effectors: Chemokines | | | | | |
| IL-8 | pg/ml | 4.4 (2.4, 10.4) | 6.1 (3.4, 13.3) | 7.6 (3.8, 18.3) | 7.0 (4.0, 15.5) | <0.05 | ns |
| IP-10 | pg/ml | 107 (79, 136) | 122 (88, 171) | 102 (75, 141) | 115 (80, 158) | ns | <0.001 |
| MCP-1 | pg/ml | 124 (75, 184) | 120 (77, 184) | 113 (78, 191) | 105 (77, 174) | ns | ns |
| | | Adhesion molecules | | | | | |
| sICAM-1 | ng/ml | 133 (109, 152) | 137 (119, 169) | 149 (123, 173) | 152 (123, 191) | <0.0005 | <0.005 |
| sVCAM-1 | ng/ml | 386 (301, 481) | 389 (303, 489) | 376 (295, 467) | 394 (330, 495) | ns | ns |
| | | Fas-mediated pathway | | | | | |
| sFasL | pg/ml | 0.12 (0.08, 0.19) | 0.13 (0.07, 0.20) | 0.12 (0.08, 0.18) | 0.11 (0.06, 0.16) | ns | ns |
| sFas | ng/ml | 3.8 (3.0, 4.7) | 4.5 (3.7, 5.5) | 4.5 (3.6, 5.6) | 5.4 (3.7, 6.9) | <0.0001 | <0.0001 |
| | | Other inflammatory markers | | | | | |
| CRP | µg/ml | 1.2 (0.5, 3.2) | 1.1 (0.6, 2.7) | 1.4 (0.5, 3.9) | 1.6 (0.8, 3.2) | <0.05 | ns |
| IL-6 | pg/ml | 0.8 (0.6, 1.4) | 0.9 (0.7, 1.5) | 0.8 (0.4, 1.3) | 0.9 (0.6, 2.2) | ns | ns |

Data are medians (quartiles); analyses were done on concentrations transformed to their logarithms.
*P-value for the albuminuria main effect in an ANOVA;
†P-value for the cC-GFR main effect in an ANOVA;

These markers were studied further by examining their correlations with each other, and with the two nephropathy measures, cC-GFR and AER (Table 4). The negative correlations between the six markers and cC-GFR recapitulate the negative associations shown in Table 3 and FIG. 1. All pairs of markers are significantly correlated, but the coefficients are generally modest. Only the correlation of the two receptors (sTNFR1 and sTNFR2) with cC-GFR and with each other exceeded 0.50. Note the poor (although significant) correlations between TNFα and its receptors (r=0.11 for TNFα/sTNFR1 and r=0.20 for TNFα/sTNFR2).

TABLE 4

Spearman correlation coefficients between cC-GFR, AER, and serum markers of inflammation and apoptosis in the study group

| | AER | TNFa | sTNFR1 | sTNFR2 | sFas | IP-10 | sICAM |
|---|---|---|---|---|---|---|---|
| cC-GFR | −0.31 | −0.15 | −0.57 | −0.56 | −0.27 | −0.13* | −0.17 |
| AER | 1.00 | 0.11 | 0.41 | 0.28 | 0.04‡ | −0.12† | 0.20 |
| TNFa | | 1.00 | 0.11* | 0.20 | 0.34 | 0.19 | 0.17 |
| sTNFR1 | | | 1.00 | 0.81 | 0.26 | 0.20 | 0.21 |
| sTNFR2 | | | | 1.00 | 0.32 | 0.26 | 0.27 |
| sFas | | | | | 1.00 | 0.14* | 0.12* |
| IP-10 | | | | | | 1.00 | 0.14* |
| sICAM | | | | | | | 1.00 |

*p < 0.01,
†p < 0.05
‡p = ns,
otherwise all other p < 0.0001.

The independence of the associations of these six markers of inflammation or apoptosis with cC-GFR was examined in multiple regression models. Only sTNFR1, sTNFR2 and sFAS remained significant when all were included in the model. Although sTNFR2 was statistically significant in this model, its contribution was small due to its high collinearity with sTNFR1, so it was not retained in subsequent modeling. Most notable about this model was that the serum markers alone (sTNFR1 and Fas) explained 41% of the variation in cC-GFR (adjusted r2) and addition of age and AER to the model increased the adjusted r2 to only 45% (Table 5). Addition of the other clinical covariates from Table 2 did not improve the adjusted $r^2$. The relative influence of these covariates on cC-GFR is summarized in Table 5 by the cC-GFR estimated at the 25th, 50th and 75th percentiles of each covariate, with and without adjustment for other covariates.

TABLE 5

Mean cC-GFR at the $25^{th}$, $50^{th}$ and $75^{th}$ Percentiles of Each Significant Covariate and the Corresponding Estimates Adjusted for the Other Covariates

| Covariate | Percentile | Univariate analysis | | Multivariate analysis * | |
|---|---|---|---|---|---|
| | | cC-GFR (ml/min/ 1.73 m$^2$) | p-value | cC-GFR (ml/min/ 1.73 m$^2$) | p-value |
| Age [y] | | | <0.0001 | | <0.002 |
| 31 | $25^{th}$ | 115 | | 114 | |
| 40 | $50^{th}$ | 109 | | 112 | |
| 48 | $75^{th}$ | 104 | | 110 | |
| AER [µg/min] | | | <0.0001 | | <0.000 |
| 22 | $25^{th}$ | 119 | | 115 | |
| 39 | $50^{th}$ | 111 | | 112 | |
| 79 | $75^{th}$ | 102 | | 108 | |
| sTNFR1 [pg/ml] | | | <0.0001 | | <0.000 |
| 1216 | $25^{th}$ | 121 | | 120 | |
| 1442 | $50^{th}$ | 112 | | 112 | |
| 1764 | $75^{th}$ | 101 | | 103 | |
| sFas [pg/ml] | | | <0.0001 | | <0.008 |
| 3.63 | $25^{th}$ | 112 | | 113 | |
| 4.50 | $50^{th}$ | 110 | | 112 | |
| 5.72 | $75^{th}$ | 107 | | 111 | |

* Adjusted $r^2$ for the multivariate model was 0.45, whereas it was 0.41 after adjustment for sTNFR1 and sFas only. Adjustments for gender, HbA1c, bmi, anti-hypertensive and lipid-lowering treatment, and duration of storage samples did not modify the associations significantly.

The effect on cC-GFR is the most pronounced for sTNFR1, and it is hardly changed by multivariate adjustment. Adjustment for the other potentially relevant clinical covariates—such as gender, hemoglobin A1c, body mass index, renoprotective and other antihypertensive treatment and lipid-lowering treatment, and duration of storage of serum specimens did not modify the association of sTNFR1 and Fas with cC-GFR. When the analysis was repeated using sTNFR2 instead of sTNFR1, the result was similar, indicating that measurement of either receptor yields roughly the same information.

The primary focus of this study was on cC-GFR (not albuminuria) as an outcome in early diabetic nephropathy and its attempt to differentiate the observed effect of markers on GFR from their potential associations with AER. Both uni- and multivariate analyses were performed. In univariate analyses, six markers were unrelated to renal function (CRP, IL-6, IL-8, MCP-1, sVCAM-1, and sFasL) and six were significantly associated with variation in cC-GFR (TNFα, sTNFR1, sTNFR2, sFas, sICAM-1, and IP10). Among the six, the associations of TNF receptors with decreased cC-GFR were the strongest.

Based on multivariate analysis, of the six markers, only the concentrations of sTNFR1, sTNFR2 and sFas contributed independently to cC-GFR. The effect of TNF receptors on cC-GFR was much more pronounced than the effects of clinical covariates as age and AER (Table 5). Furthermore, serum concentrations of sTNFR1 and sTNFR2 are highly correlated (Spearman r=0.81) and show roughly the same associations with cC-GFR.

This study provides evidence for the first time that markers of TNFα- and Fas-mediated pathways are strongly associated with variation in cC-GFR in patients with T1DM and early diabetic nephropathy. This association is independent of the association of these markers with AER. These findings support the hypothesis that inflammation and apoptosis are involved in early renal function decline in T1DM.

Other cross-sectional studies in T1DM reported that serum concentrations of TNFα-related markers were elevated in comparison with healthy subjects and that the higher concentrations of these markers were associated with elevated urinary albumin excretion (Zoppini, supra, and Schram et al., Diabetologia, 48:370-378, 2005). Cross-sectional association between serum concentrations of sTNFRs and variation in GFR has been shown in T2DM (Lin et al., Kidney. Int., 69:336-342, 2006) as well as in non-diabetic individuals (Keller et al., Kidney. Int., 71:239-244, 2007 and Knight et al., J. Am. Soc. Nephrol., 15:1897-1903, 2004). In the prospective CARE study, high serum concentrations of sTNFR2 were found to be associated with faster progression of renal function loss (Tonelli et al., Kidney. Int., 68:237-245, 2005). However, all subjects in that study had chronic kidney disease (GFR<60 ml/min/1.73 m$^2$) at baseline.

One may argue that the association of TNFα receptors and cC-GFR simply reflects impaired renal handling of these proteins. Indeed, these receptors are cleared mainly by the kidneys as shown by tracer studies of radiolabelled sTNFR2 in animals (Bemelmans et al., Cytokine, 6:608-615, 1994). Also serum concentrations of soluble TNF receptors increase in advanced renal failure, as demonstrated in bi-nephrectomized mice (Bemelmans, supra) and in human studies (Brockhaus et al., Kidney. Int., 42:663-667, 1992). However, the majority of patients in this study had normal renal function, and even the renal function loss resulting from uni-nephrectomy does not raise serum sTNF receptor concentrations in animals. Moreover, serum concentrations of sFasL, which has a molecular mass similar to soluble TNF receptors, is not associated with cC-GFR, while the receptors are strongly associated with variation in cC-GFR. Based on those data potentially decreased clearance of those molecules is not the most likely explanation of these findings.

Adhesion molecules and chemokines are potential downstream effectors of the TNF-sTNFRs inflammatory pathway (Segerer, supra). Expression of IL-8, MCP-1, and IP-10 mRNA is induced in TNFα-activated PBMNC taken from individuals with diabetes, but not from healthy ones (Wong, supra). Expression and serum concentrations of chemokines and adhesion molecules, VCAM-1 and ICAM-1, increase as diabetic nephropathy develops (Wong, supra, and Nelson et al., Nephrol. Dial. Transplant., 20:2420-2426, 2005). In the univariate analysis described here, serum concentrations of IP-10 and sICAM-1 were associated with variation in cC-GFR and they correlated with their potential upstream regulators. Nevertheless, the observed effects were weak, and disappeared in multivariate analysis, as one would expect if their effect were not independent of the TNF receptors or sFas.

Analysis of the Fas-mediated pathway revealed an independent effect of the serum concentration of sFas on variation in cC-GFR and a lack of an effect of the serum concentration of sFasL. A similar pattern of disparate effects of sFas and sFasL was previously demonstrated in individuals with advanced kidney disease (Perianayagam, supra). Also, in a small number of individuals with T1DM and without proteinuria, sFas was reported to correlate with both ACR and GFR (Protopsaltis et al., Med. Princ. Pract., 16:222-225, 2007).

The mechanism of action of soluble Fas receptor has not been well known but may be similar to that of TNF receptors in that it leads to an enhanced Fas-mediated response in the kidney. The Fas-related system is involved mainly in regulation of apoptosis (Schelling, supra), whereas the TNF-system regulates apoptotic and inflammatory responses. Consistent with this is the tubulointerstitial apoptosis seen in strepotozocin-induced diabetic rats (Kumar, supra) and in human diabetic kidneys (Kumar, supra). Some evidence also suggests that TNFα may induce Fas-mediated apoptosis (Elzey et al., J. Immunol. 167:3049-3056, 2001 and Boldin et al., J. Biol. Chem., 270:387-391, 1995). In this study serum concentrations of TNFα and sFas were markedly correlated.

The relatively poor correlations between TNFα and its receptors may have resulted from low detection of TNFα bound to its receptors and its association with cC-GFR being weaker than that of its receptors.

In conclusion, this study provides the first clinical evidence that markers of the TNF- and Fas-mediated pathways are strongly associated with glomerular filtration rate in patients with T1DM and NA or MA. sTNFR1, sTNFR2 and sFas are the markers representing these associations most strongly.

Example 2: Serum Concentrations of TNFa, Soluble TNF Receptor Type 1 and 2 and Fas Predict Strongly Early Renal Function Decline in Human Subjects with Type 1 Diabetes and No Proteinuria and Carry Strong Diagnostic Potential Glomerular filtration rate (GFR) starts to decline before proteinuria occurs in type 1 diabetes (Perkins et al., J Am Soc Nephrol. 18:1353-1361, 2007). This phenomenon is referred to as "early renal function decline" (ERFD). The clinically approved diagnostic marker for progression of diabetic nephropathy, microalbuminuria (MA), does not predict renal function decline sufficiently at this early stage. First, the presence of MA is not necessary for renal function decline to occur. Second, only a proportion of people with MA develop renal function decline (Perkins et al., 2007, supra). There is an urgent need for novel diagnostic tools that can identify patients at high risk of progression and to implement enhanced therapeutic strategies.

In the population of 667 patients with type 1 diabetes and no proteinuria described in Example 1, serum concentrations of TNFa, soluble TNF receptor type 1 (STNFR1), soluble TNFR2, and soluble Fas were associated with lower GFR in the cross-sectional phase. The next prospective phase of the study included the subset of 398 patients who were followed for 3-5 years. Serum concentrations of TNFa, sTNFR1, sTNFR2 and Fas emerged as strong predictors of GFR decline with strength at least comparable to microalbuminuria. Repeated measurements over time were performed to evaluate intraindividual variation and their impact on the prediction.

Figure 2A:
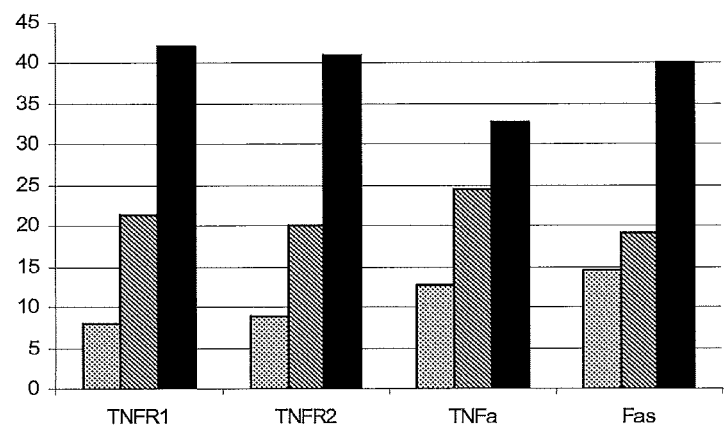
FIGS. 2A-2B are bar graphs showing the proportion of the event=renal function loss defined as the top quartile of the fastest progression in the prospective 2nd Joslin Kidney Study (2A) and in the replicative 1st Joslin Kidney Study (2B), stratified by tertiles of the respective marker.
Figure 2B:
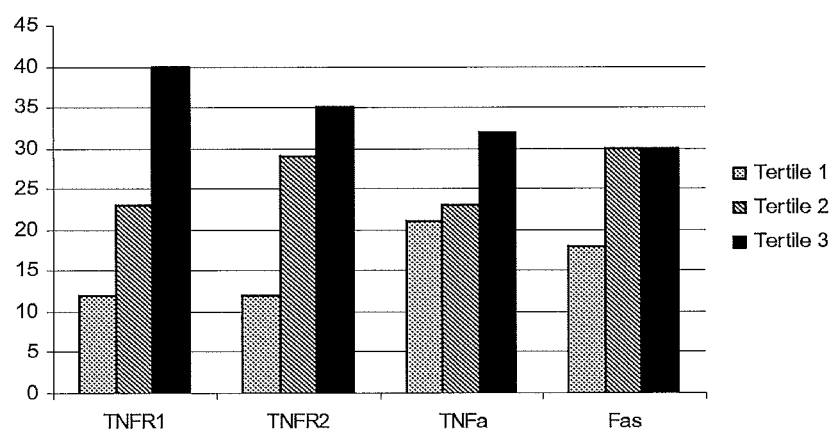
Figure 3A:
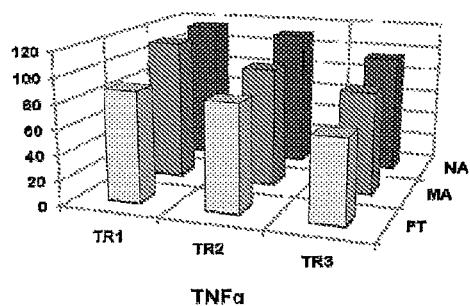
FIGS. 3A-3D are 3-D bar graphs showing adjusted mean GFR (ml/min/1.73 m$^2$) in subjects with Type-2 Diabetes according to Albumin excretion rate status (NA=normoalbuminuria, MA=microalbuminuria, and PT=proteinuria) and tertile (T1, T2, T3): 3A, TNFα; 3B, IL6; 3C, sTNFR1; 3D, sFas.
Figure 3B:
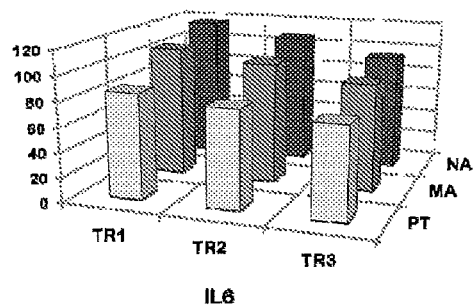
Figure 3C:
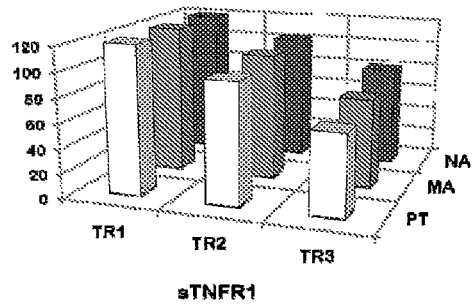
Figure 3D:
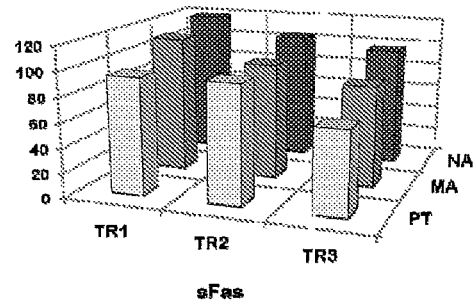
Figure 4:
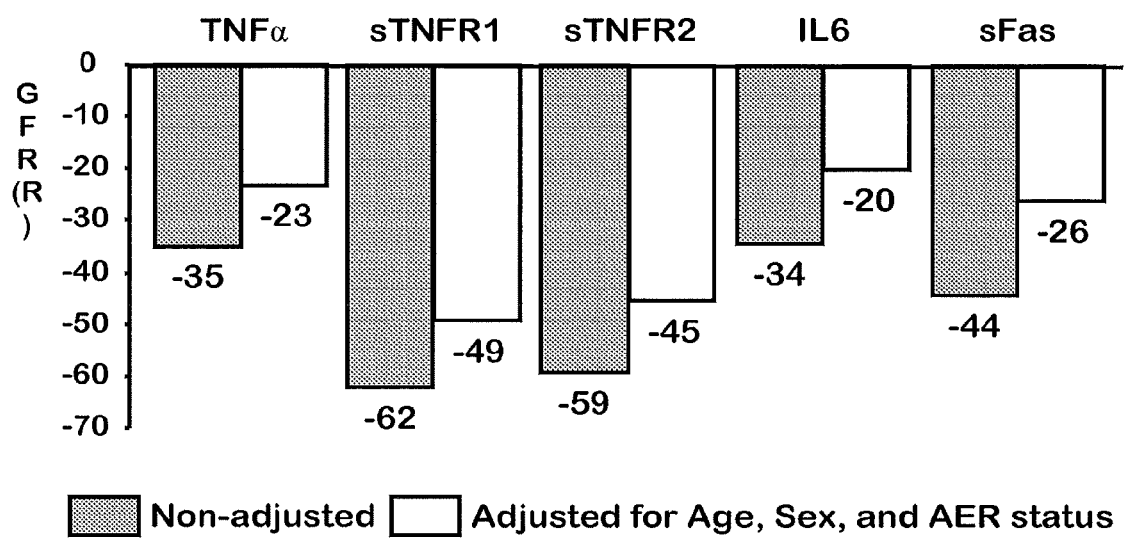
FIG. 4 is a bar graph showing the association between TNFα, sTNFR1, sTNFR2, IL-6, and sFas in subjects with type II diabetes. Data shown the difference in mean GFR (ml/min/1.73 m$^2$) between the highest, and the lowest tertiles of five markers (TNFα, sTNFR1, sTNFR2, IL6, and sFas) in the crude analysis after adjustment for age, gender, and AER status.

To validate these findings the study was replicated in an independent population sample of type 1 diabetic population from the 1st Joslin Kidney Study (n=299, observation period 8-12 years). The results, shown in FIGS. 2A-2B, demonstrated that the predictive effect of those four markers is comparably strong.

In summary, the association of serum concentrations of TNFa, STNFR1, STNFR2, and sFas with ERFD were validated in subjects with type 1 diabetes in the cross-sectional study (see Example 1), a prospective study that included repeated measurements and consideration of the confounding clinical factors, and were further replicated in the independent population sample. This strongly demonstrates that implementation of those markers will significantly strengthen diagnostic algorithm to identify subjects with type 1 diabetes and early diabetic nephropathy at high risk of renal function decline.

The former studies on inflammatory markers focused on albumin excretion, or on much more advanced stages of diabetic nephropathy. The present results demonstrate the strong diagnostic potential of those markers for GFR prediction, rather than albuminuria; as discussed above, GFR is a much more accurate marker of ERFD than is albuminaria. Furthermore, these results (i.e., the prospective and replication studies) demonstrate the usefulness of these markers in the very early stages of diabetic nephropathy.

Example 3: Serum Concentrations of TNFα, Soluble TNF Receptor Types 1 and 2, Soluble Fas, and IL-6 Predict Renal Function Decline in Human Subjects with Type 2 Diabetes Subject Selection The study group included 404 individuals with type 2 diabetes and normoalbuminuria (NA), microalbuminuria (MA), and proteinuria (PT), attending the Joslin clinic. Study group characteristics, sorted according to Albumin Excretion Rate (AER), are shown in Table 6.

TABLE 6

Characteristics of the study group according to AER status.

| Characteristics | NA (n = 217) | MA (n = 127) | PT (n = 60) |
| --- | --- | --- | --- |
| Age (yr) | 55 ± 10 | 56 ± 9 | 58 ± 10 |
| DM Duration (yr) | 12 ± 8 | 14 ± 8 | 16 ± 8 |
| cC-GFR (ml/min/1.73 m2) | 110 ± 30 | 95 ± 34 | 76 ± 32 |
| cC-GFR categories | | | |
| >120 ml/min | 32.3% | 22.1% | 13.3% |
| >90 ml/min | 44.2% | 29.9% | 15.0% |
| 60 to 89 ml/min | 19.8% | 32.3% | 36.7% |
| <60 ml/min | 3.7% | 15.8% | 35.0% |

Serum Marker Analysis

Serum concentrations of TNFα, soluble TNF receptor 1 (sTNFR1), soluble TNF receptor 2 (sTNFR2), soluble intercellular and vascular adhesion molecules (sICAM-1 and sVCAM-1, respectively), soluble Fas (sFas), IL-6, and CRP were measured in each of the subjects by ELISA or using the Luminex® platform. Results are shown below.

TABLE 7

Median plasma concentrations of biomarkers of inflammation, apoptosis, and endothelial function according to AER status and group-specific median GFR.

| Plasma markers | NA | | MA | | PT | | Group Contrast | |
|---|---|---|---|---|---|---|---|---|
| | GFR >108 (n = 111) | GFR ≤108 (n = 106) | GFR >91 (n = 64) | GFR ≤91 (n = 63) | GFR >71 (n = 30) | GFR ≤71 (n = 30) | AER P | GFR P |
| TNFα (pg/mL) | 3.3 | 5.1 | 3.5 | 6.4 | 5.2 | 5.3 | <0.05 | <0.0001 |
| sTNFR1 (pg/mL) | 1009 | 1394 | 1162 | 1891 | 1516 | 2707 | <0.0001 | <0.0001 |
| sTNFR2 (pg/mL) | 1913 | 2614 | 2236 | 3416 | 2959 | 4801 | <0.0001 | <0.0001 |
| sFas (pg/mL) | 5.0 | 6.8 | 5.3 | 7.7 | 7.2 | 9.3 | <0.0001 | <0.0001 |
| OPG (pg/mL) | 279 | 377 | 316 | 425 | 359 | 476 | <0.0001 | NS |
| OPN (pg/mL) | 825 | 1080 | 1013 | 1716 | 1835 | 2918 | <0.005 | NS |
| IL6 (pg/mL) | 1.1 | 2.0 | 2.0 | 2.4 | 2.2 | 2.4 | <0.0001 | <0.001 |
| CRP (mg/L) | 1.8 | 4.0 | 4.1 | 3.9 | 3.7 | 5.0 | <0.0005 | NS |
| sICAM-1 (ng/mL) | 161 | 179 | 172 | 181 | 191 | 176 | <0.01 | NS |
| sVCAM-1 (ng/mL) | 450 | 481 | 404 | 481 | 481 | 523 | <0.05 | NS |

TABLE 8

Spearman correlation coefficients among plasma biomarkers of inflammation, apoptosis, and endothelial function.

| | TNFα | sTNFR1 | sTNFR2 | IL6 | CRP | sFas | OPG | OPN | sICAM-1 | sVCAM-1 |
|---|---|---|---|---|---|---|---|---|---|---|
| GFR | -0.48* | -0.84* | -0.79* | -0.42* | -0.23* | -0.58* | -0.44* | -0.27* | -0.21* | -0.27* |
| TNFα | 1.00 | 0.49* | 0.54* | 0.28* | 0.15‡ | 0.47* | 0.38* | 0.17† | 0.31* | 0.34* |
| sTNFR1 | | 1.00 | 0.89* | 0.51* | 0.29* | 0.68* | 0.46* | 0.24* | 0.31* | 0.33* |
| sTNFR2 | | | 1.00 | 0.47* | 0.27* | 0.65* | 0.41* | 0.19† | 0.34* | 0.38* |
| IL6 | | | | 1.00 | 0.58* | 0.34* | 0.33* | 0.05 | 0.33* | 0.13§ |
| CRP | | | | | 1.00 | 0.12§ | 0.26* | -0.05 | 0.25* | -0.11§ |
| sFas | | | | | | 1.00 | 0.53* | 0.24* | 0.33* | 0.36* |
| OPG | | | | | | | 1.00 | 0.15‡ | 0.29* | 0.28* |
| OPN | | | | | | | | 1.00 | 0.05 | 0.27* |
| sICAM-1 | | | | | | | | | 1.00 | 0.22* |
| sVCAM-1 | | | | | | | | | | 1.00 |

A cross sectional analysis of the data presented in Tables 7-8 was performed. Specifically, marker levels were analyzed in 364 individuals from the group shown in Table 6 with GFR greater than or equal to 60 mL/minute/1.73 m$^2$ and either normal urinary albumin excretion (NA; n=217 of 346) or microalbuminuria (MA; n=129 of 346). The data is shown in Table 9. None of these subjects tested exhibited signs of ischemic heart disease.

TABLE 9

Median Plasma Concentrations of Markers of Inflammation or Apoptosis according to AER and GFR.

| | Normoalbumuria | | Microalbuminuria | |
|---|---|---|---|---|
| Plasma marker | cC-GFR >118 n = 106 | cC-GFR <118 n = 105 | cC-GFR >107 n = 58 | cC-GFR <107 n = 55 |
| TNFα (pg/mL) | 3.3 | 4.7 | 3.4 | 5.3 |
| sTNFR1 (ng/mL) | 1.0 | 1.3 | 1.2 | 1.8 |
| sTNFR2 (ng/mL) | 1.9 | 2.6 | 2.2 | 3.1 |
| sFas (pg/mL) | 5.0 | 6.5 | 5.2 | 7.6 |
| IL-6 (pg/mL) | 1.1 | 1.9 | 2.0 | 2.2 |

P = 0.0001

As shown above, higher concentrations of TNFα, sTNFR1, sTNFR2, sFas, and IL-6 were strongly associated with lower GFR in NA subjects and MA subjects. These associations remained highly significant (p<0.0001) after adjustment for age, gender, and albuminuria status. The associations between GFR and CRP, sICAM-1, and sVCAM-1 were borderline significant.

These observations suggest that serum evaluation of the markers TNFα, sTNFR1, sTNFR2, sFas, and IL-6 can be used to predict ERFD in type 2 diabetics with NA and MA.

Example 4: Serum Concentrations of Soluble TNF Receptor 1 Predicts End Stage Renal Disease in Subjects with Baseline Proteinuria Subject Selection 434 subjects attending Joslin Diabetes Clinic with type 1 diabetes and baseline proteinuria were followed for an average of 8 years and progression to end-stage renal disease (ESRD) as an outcome has been evaluated.

Serum Marker Analysis

Serum concentrations of soluble TNF receptor 1 (sTNFR1) were measured using ELISA. The associations between the serum levels of sTNFR1 and end stage renal disease controlled for the baseline stage of chronic kidney disease was then assessed. Results are shown in Table 10.

TABLE 10 sTNFR1 Levels in Subjects with Baseline Proteinuria

| TNFR1 [pg/ml] | ESRD | Subject no. | Median | Q1 | Q3 |
|---|---|---|---|---|---|
| CKD <3 | 0 | 213 | 2078 | 1728 | 2437 |
|  | 1 | 28 | 2242 | 1756 | 3062 |
| CKD = 3 | 0 | 78 | 3199 | 2719 | 3899 |
|  | 1 | 46 | 4156 | 3172 | 4772 |
| CKD >3 | 0 | 9 | 5518 | 4869 | 8327 |
|  | 1 | 60 | 6605 | 5402 | 7590 |

As shown in Table 10, serum levels of sTNFR1 are associated with CKD (as assessed by GFR) and ESRD. The association between sTNFR1 and ESRD remained significant after adjustment for baseline stage CKD.

These observations support that sTNFR1 can be used to predict the progression of diabetic nephropathy. Furthermore, these observations support that sTNR1 can be used to predict ESRD in patients with type 1 diabetes and proteinuria.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of determining whether a human subject has an increased risk of developing chronic kidney disease (CKD), or end stage renal disease (ESRD), or both, the method comprising:
    obtaining a sample from a human subject who has normoalbuminuria (NA), microalbuminuria (MA), or proteinuria (PT);
    detecting the presence of and measuring the level of soluble TNF receptor type 1 (sTNFR1) in the subject sample with an anti-sTNFR1 antibody and detecting binding and measuring the level of binding between sTNFR1 and the antibody; comparing the subject levels of sTNFR1 with reference levels of sTNFR1; determining whether the subject has an increased risk of developing CKD or ESRD, or both, based on the comparison of the subject levels with the reference levels, wherein the presence of sTNFR1 in the subject sample at levels that are significantly higher than the reference levels indicates that the subject has an increased risk of developing CKD, ESRD, or both; and
    administering a therapy to any subjects identified as having an increased risk of developing CKD or ESRD and monitoring said identified subjects for a reduction in the level of sTNFR1.

2. The method of claim 1, wherein the subject has Type 1 or Type 2 diabetes.

3. The method of claim 1, wherein the sample comprises serum from the subject.

* * * * *